United States Patent [19]

Borggrefe et al.

[11] 4,153,726

[45] May 8, 1979

[54] SKIN PROTECTION AGENTS CONTAINING POLYETHERCARBOXYLIC ACIDS

[75] Inventors: Gerhard Borggrefe, Düsseldorf; Hinrich Möller, Düsseldorf-Benrath; Peter Lorenz, Langenfeld; Rainer Osberghaus, Düsseldorf-Urdenbach; Christian Gloxhuber, Haan; Siegfried Braig, Hilden, all of Fed. Rep. of Germany

[73] Assignee: Henkel Kommanditgesellschaft auf Aktien (Henkel KGaA), Düsseldorf, Fed. Rep. of Germany

[21] Appl. No.: 544,809

[22] Filed: Jan. 28, 1975

[30] Foreign Application Priority Data

Jan. 29, 1974 [DE] Fed. Rep. of Germany ....... 2404047

[51] Int. Cl.² .................. A61K 31/225; A61K 31/23
[52] U.S. Cl. ..................... 424/313; 424/315; 424/316; 424/317; 424/365
[58] Field of Search ............... 424/315, 316, 317, 365, 424/313

[56] References Cited

U.S. PATENT DOCUMENTS

| | | | |
|---|---|---|---|
| 2,311,008 | 2/1943 | Tucker | 260/535 P |
| 3,293,176 | 12/1966 | White | 260/535 P |
| 3,725,290 | 4/1973 | Nelson et al. | 260/535 P |

FOREIGN PATENT DOCUMENTS 1447188  6/1966  France ..................................... 424/365

OTHER PUBLICATIONS

Chem. Abs., 1968, vol. 68, pp. 40559z.
Chem. Abs., 1970, vol. 73, pp. 28779s.

*Primary Examiner*—Dale R. Ore
*Attorney, Agent, or Firm*—Hammond & Littell

[57] ABSTRACT

Skin-care and skin-protection agents contain at least one polyethercarboxylic acid as a skin moisture-containing agent, and a process for treating skin comprises applying an effective amount of these agents to the skin.

3 Claims, No Drawings

SKIN PROTECTION AGENTS CONTAINING POLYETHERCARBOXYLIC ACIDS

THE PRIOR ART

It is generally known that the protective measures for healthy skin include among other things, a certain hygroscopicity. The substances, on which this hygroscopicity and its constant restoration depend, may be removed from the skin by environmental influences, such as repeated washing with substances which have a strong wetting and extracting effect, and the influence of chemicals or severe weather. The result of this removal produces alterations in the horny layer which can greatly reduce the protective action of the skin against harmful environmental influences.

Objects of the Invention

An object of the present invention is to provide skin-care and skin protection agents, by means of which the functional capacity of the skin may be maintained or increased in spite of harmful environmental influences, and which effectively support the restoration of the horny layer, should any damage have been incurred.

Another object of the present invention relates to skin-care and skin-protection agents containing at least one polyethercarboxylic acid as a skin moisture-containing (i.e., as moisturizing) agent.

These and further objects of the present invention will become more apparent as the description thereof proceeds.

DESCRIPTION OF THE INVENTION

The present invention relates to skin-care and skin-protection agent composition containing at least one polyethercarboxylic acid as a skin moisture-containing agent, as well as relating to a method for treating skin comprising applying an effective amount of this composition to the skin.

Accordingly the present invention provides skin-care and skin-protection composition comprising conventional constituents, such as emulsifiers, fatty substances, plant extracts, solvents, perfumes, thickeners and preservatives in the customary amounts and at least one polyethercarboxylic acid, or salt thereof, of the general formula $$R_1-O-CH_2-COOM,$$

in which M is hydrogen, an alkali metal cation or an alkaline earth metal cation, an ammonium ion, an alkyl substituted or alkylol substituted ammonium ion, and $R_1$ is straight-chain, or branched-chain, alkyl having 1 to 8 carbon atoms, in which said alkyl can have one or more carboxyl groups, one or more hydroxyl groups and/or one or more groups of the formula $-O-CH_2-COOM$, in which M has the above-defined meanings, with the proviso that at least 2 carboxyl groups are present in the molecule, said acid or salt being present in an amount of from 1% to 20% by weight, preferably 3% to 10% by weight, based upon the total weight of the composition.

More particularly, the present invention provides a cosmetic agent composition for the care and protection of the skin of a warm-blooded animal consisting essentially of from about 1% to about 20% by weight, based upon the total weight of at least one polyethercarboxylic acid compound having the formula $$R_1-O-CH_2-COOM$$

wherein M is selected from the group consisting of hydrogen, an alkali metal cation, an alkaline earth metal cation, ammonium ion, a lower-alkyl-ammonium ion, a lower-alkanol-ammonium ion, and the mixtures thereof, wherein $R_1$ is alkyl having 1 to 8 carbon atoms and having substituents selected from the group consisting of at least one carboxyl, at least one hydroxyl and at least one group of the formula $-O-CH_2-COOM$, where M has the abovedefined meanings, with the proviso that there are at least two carboxyl groups in the molecule of said acid compound and the remainder being inert cosmetic excipients for the care and protection of the skin.

In addition, the present invention provides an improvement in a process for the care and protection of the skin of warm-blooded animals comprising topically applying to the skin a safe but effective amount of agent composition mentioned above.

The polyethercarboxylic acids, or salts thereof, which are to be used in accordance with the invention are extremely suitable for maintaining or restoring the water retention of the skin and thus for keeping the skin soft, supple and fully capable of performing its function.

These acids can be produced according to generally known processes. Thus bis-O-carboxymethyl-glycol,-tris-O-carboxymethyl-glycerin, O-carboxymethyl-tartronic-acid, O-carboxymethyl-malic acid, bis-O-carboxymethyl-tartaric acid, O-carboxymethyl-citric acid, tris-O-carboxymethyl-1,1,1-trimethylolpropane, tris-O-carboxymethyl-1,1,1-trimethylolethane are prepared in accordance with U.S. patent application Ser. No. 221,815 filed Jan. 28, 1972 in which compounds of the formula $$[R-\underset{\underset{(CH_2)_n-Y}{|}}{\overset{\overset{(CH_2)_n-X}{|}}{C}}-(CH_2)_n-OH]_z,$$

in which X and Y are each hydroxyl or ester groups, R is hydrogen, alkyl having 1 to 2 carbon atoms or $-(CH_2)_n-(OCH_2)_m-COOH$, m and n are the intergers 0 or 1, and z is the integer 0, 1 or 2, with the proviso that the carbon atom which is attached to R has a maximum of one hydroxyl group, are reacted with diazoacetic acid esters in the presence of Lewis acids, and the reaction products are saponified.

The compounds 1,2-bis-O-carboxymethyl-glycerin, mono-O-carboxymethyl-glyceric acid, mono-O-carboxymethyl-tartaric acid, mono-O-carboxymethyl-erythronic acid, mono-O-carboxymethyl-1,2,3-trioxyglutaric acid, 1,2bis-O-carboxymethyl-1,2,3,-trioxyglutaric acid can be produced according to the disclosure of U.S. patent application Ser. No. 221,816 filed Jan. 28, 1972 now U.S. Pat. 4,002,676, in which compounds of the general formula $$\underset{\underset{R_3-CH-X}{|}}{\overset{\overset{R_2-CH-X}{|}}{[HC-X]_n}},$$

in which $R_2$ and $R_3$ independent on one another are hydrogen or ester groups, X is hydroxyl or halogen, n is the integer 0 or 1, and which contain at least 2 hydroxyl groups, are reacted in the presence of Lewis acids with diazoacetic acid ester in the molar ratio 1:1 to 1:(p-1), wherein p is the number of hydroxyl groups, and the reaction products are saponified.

Examples of polyethercarboxylic acids which can be used in accordance with the invention are diglycolic acid, O-carboxymethyl-lactic acid, bis-O-carboxymethyl-glycol, tris-O-carboxymethyl-glycerin, O-carboxymethyl-tartronic acid, O-carboxymethyl-malic acid, bis-O-carboxymethyl-tartaric acid, O-carboxymethyl-citric acid, tris-O-carboxymethyl-1,1,1-trimethylol-propane, tris-O-carboxymethyl-1,1,1-trimethylolethane, 1,2-bis-O-carboxymethyl-glycerin, mono-O-carboxymethyl-glyceric acid, mono-O-carboxymethyl-tartaric acid, mono-O-carboxymethyl-erythronic acid, mono-O-carboxymethyl-1,2,3-trihydroxyglutaric acid, 1,2-bis-O-carboxymethyl-1,2,3-trihydroxyglutaric acid. They are primarily used in the form of their salts in the skin-care and skin-protection compositions of the invention.

Substances which are suitable as cations of the salts of the polyethercarboxylic acids which are to be used are the alkali metal salts such as sodium or potassium, alkaline earth metal salts, the ammonium salt, the lower-alkyl substituted ammonium salts as methylammonium, ethylammonium, propylammonium, isopropylammonium, dimethylammonium, diethylammonium, and the lower alkylol substituted ammonium salts such as monoethylolammonium, diethylolammonium, triethylolammonium, and isopropylolammonium. The alkali metal salts are preferred, and especially prepared are the sodium salts.

All the afore-mentioned salts constitute colorless, odorless and completely stable products, which possess excellent compatibility and have no disadvantageous side effects on the skin-care and skin-protection agent compositions which are mixed with them.

It is known that in addition to other factors a certain hygroscopicity is necessary for the protection of a healthy skin. If the skin is deprived of the substances which are responsible for this hydroscopicity as well as its continual restoration by environmental circumstances such as repeated washings, effect of chemicals or strong weather influences, alterations occur in the stratum corneum, as a result of which the protective effect of the skin against harmful influences of the environment may be considerably diminished.

It was found that the functional capacity of the skin may be maintained or restored even to a higher degree than before if it is treated with agents for the care and protection of the skin, which besides the customary constituents include from 1% to 20% by weight, preferably 3% to 10% by weight, based on the total composition of the polyethercarboxylic acids or salts used in accordance with the invention.

Among the compositions for the care and protection of the skin having special skin-caring properties due to the addition of the polyethercarboxylic acids used in accordance with the invention or their physiologically-compatible salts are emulsions of oil-in-water or water-in-oil type. These are the conventional day creams, night creams and nourishing creams, skin protection creams, glycerol creams, creams with special additives of animal or vegetable origin, sun protection or sun tanning creams, and sun protection emulsions, face lotions and after-shave lotions. The incorporation of the agents for care and protection of the skin may take place in the known manner by simple stirring-in or dissolving. In addition to the polyethercarboxylic acids or salts used in accordance with the invention, the cosmetic preparations may contain the constituents normally present in them such as emulsifiers, fatty substances, plant extracts, preservatives, perfumes, solvents, thickeners and preservatives in the customary amounts. The pH value of the agents for the care and protection of the skin may be in the acid to neutral region (pH 5—7.0) and is approximately adjusted to weakly acid values of about pH 6.

The following examples are merely illustrative of the present invention without, however, being deemed limitative in any manner thereof.

EXAMPLES

The following compounds are representative examples of the polyethercarboxylic acids, which are to be used in accordance with the invention as skin moisture-containing agent compositions, and were subjected to the tests described below and were used in recipes described below:

Product A: Diglycolic acid, sodium salt
Product B: Bis-O-carboxymethyl-glycol, sodium salt.
Product C: Mono-O-carboxymethyl-tartaric acid, sodium salt.
Product D: O-carboxymethyl-lactic acid, sodium salt.
Product E: O-carboxymethyl-tartronic acid, sodium salt.

The favorable action of the compounds, which are to be used in accordance with the invention, with regard to capacity for the absorption and retention of water, was also determined by means of test methods which are described more fully hereinafter. A process for determining the equilibrium dampness, which contitutes a gauge for the water retention capacity, and the determination of the water retention, rehydration and elasticity of impregnated pig epidermis is described in these tests.

1. Determination of the Equilibrium Dampness

The substances (about 300 to 500 mg) to be tested were moistened with a defined quantity of water and exposed for 24 hours at 23° C. to various relative atmospheric humidities (1%, 30%, 47%, 65%, 89% and 100% relative humidity). The amount of water absorbed or desorbed was determined gravimetrically and plotted on a graph. The relative humidity at which neither expulsion nor retention of water is effected, can be determined from the resultant curves. This value, which is designated as the equilibrium dampness, is a gauge for the water retention capacity of a substance. The lower the value, the more positive should be the assessment of the product.

2. Tests on the Pig Epidermis

(a) To Obtain the Pig Epidermis

As soon as the pigs have been killed, the bristles of the skin are cut off by means of a shearing machine (shearing head of 0.1 mm). The pigs are soaked for 3 to 5 minutes in warm water of 60° C., the epidermis is then peeled off and stored at −20° C. until used.

(b) Determination of the Water Retention and the Rehydration of Impregnated Pig Epidermis.

Stamped out pieces of epidermis (1×2 cm) were soaked for 2 hours in a 10% solution of the test substance, excess moisture was removed by means of a small press under standardized conditions and the pieces were dried for 24 hours, hanging free between 2 clamps in a 100 ml Erlenmeyer flask at 23° C. both at 30% relative humidity and 50% relative humidity (set by sulfuric acid/water mixtures). The drying out of the impregnated test pieces to X% of the initial weight was compared with the corresponding value of the epidermis which has been soaked only in water (blank value). In Table I, the improvement in the water retention and the rehydration as compared with the blank value is given in Δ% of $H_2O$. The deviations in each double test amounted to a maximum of ±2 absolute unit. If greater deviations occured, the test was repeated. The rehydration was determined analogously by drying the pig epidermis, which has been impregnated and from which the excess moisture has been removed for 24 hours at 30% relative humidity, and by subsequent 24-hour incubation at 90% relative humidity.

(c) Gauging of elasticity of impregnated pig epidermis

Stamped out pieces of pig epidermis (1×6 cm) were soaked for 2 hours in a 10% aqueous solution of the substance which was to be tested, and excess moisture was removed from these pieces under standarized conditions. The test pieces were incubated for 24 hours, hanging free between 2 clamps both at 75% relative humidity and at 90% relative humidity and were stretched in a nipping tensile-testing machine (type: 1402) with 0 to 50 pund loading. The amount of stretch, which was measured in the Hooke range with loadings of 5 to 30 pund, was given in mm as a gauge for the elasticity.

The measured values obtained in the previously described tests can be seen hereinafter in Table. I.

TABLE I

Equilibrium dampness and measured values for pig epidermis

| | | Measurements from the pig epidermis | | | | |
|---|---|---|---|---|---|---|
| | Equilibrium dampness | Water retention Δ% $H_2O$ after drying out | | Rehydration Δ% water absorption | mm stretch with between 5 and 30 pund loading | |
| Product | (% r.h.) | at 30% r.h. | at 50% r.h. | at 90% r.h. | at 90% r.h. | at 75% r.h. |
| Blank value | — | 0 | 0 | 0 | 0.3–0.5 | 0 |
| A | 65 | 13 | 13 | 6 | 2.2 | 0.4 |
| B | 66 | 2 | 8 | 16 | 1.4 | 0.5 |
| C | 57 | — | — | 10 | 1.8 | 0.3 |
| D | 49 | 5 | 4 | 27 | 4.4 | 0.35 |
| E | — | 17 | 32 | 48 | 2.2 | 0.6 |

— = was not measured

The above Table indicates, beside the strong hygroscopicity, also the remarkable water retention capacity of the compounds in accordance with the invention, in particular when the compounds are in the form of their sodium salts.

In the following, we will give a few examples of cosmetic preparations containing substances in accordance with the invention as skin humectants.

EXAMPLE 1

| Day cream, slightly greasy | Parts by weight |
|---|---|
| Fatty acid partial glyceride Cutina MD ® Dehydag | 6.0 |
| Stearic acid | 8.0 |
| Mixture of nonionic emulsifiers Emulgin C 700 ® Dehydag | 3.0 |
| 2-octyl-dodecanol | 4.0 |
| Vegetable oil | 3.0 |
| Paraffin oil | 5.0 |
| Triethanolamine | 0.4 |
| 1,2-propylene glycol | 3.0 |
| Product A | 3.0 |
| Nipagin M | 0.2 |
| Perfume oil | 1.0 |
| Water | 63.4 |

EXAMPLE 2

| Baby cream | Parts by Weight |
|---|---|
| Mixture of higher molecular esters, mainly mixed esters of pentaerythritol fatty acid ester and citric acid fatty alcohol ester Dehymuls E ® Dehydag | 7.0 |
| Decyl oleate | 10.0 |
| Vaseline | 10.0 |
| Wool fat | 5.0 |
| Boric acid | 0.2 |
| Talcum | 12.0 |
| Zinc oxide | 8.0 |
| Nipagin M | 0.2 |
| Product B | 5.0 |
| Water | 42.6 |

EXAMPLE 3

| Night cream | Parts by Weight |
|---|---|
| Colloidally dispersed mixture of 90 parts of cetyl-stearyl alcohol and 10 parts of sodium lauryl sulfate | 10.0 |
| 2-Octyl-dodecanol | 12.0 |
| Vegetable oil | 7.0 |
| Wool fat | 2.0 |
| Glycerol | 1.0 |
| Product C | 5.0 |
| Nipagin M | 0.2 |
| Perfume Oil | 1.0 |
| Water | 61.8 |

EXAMPLE 4

| Boro-glycerol cream | Parts by Weight |
| --- | --- |
| Colloidally dispersed mixture of 90 parts of cetyl-stearyl alcohol and 10 parts of sodium lauryl sulfate | 12.0 |
| 2-Octyl-dodecanol | 8.0 |
| Vegetable oil | 5.0 |
| Boric acid | 2.0 |
| Glycerol | 28.0 |
| Nipagin M | 0.2 |
| Product D | 3.0 |
| Water | 41.8 |

EXAMPLE 5

| Sun protection cream | Parts by Weight |
| --- | --- |
| Mixture of higher molecular esters with fatty substances Dehymuls K ® Dehydag | 30.0 |
| Decyl oleate | 15.0 |
| Light protection agent | 5.0 |
| Nipagin M | 0.2 |
| Product E | 3.0 |
| Water | 46.8 |

EXAMPLE 6

| Face mask | Parts by Weight |
| --- | --- |
| Mixtures of fatty acid partial glyceride with emulsifiers Cutina LE ® Dehydag | 12.0 |
| Decyl oleate | 4.0 |
| Vitamin oil | 5.0 |
| Kaolin | 2.0 |
| Rice starch | 3.0 |
| Nipagin M | 0.2 |
| Product A | 6.0 |
| Water | 67.8 |

EXAMPLE 7

| After-shave lotion | Parts by Weight |
| --- | --- |
| Oleyl/cetyl alcohol | 1.0 |
| Ethanol 96% | 67.5 |
| Menthol | 0.2 |
| Camphor | 0.2 |
| Peru balsam | 0.1 |
| Perfume | 0.5 |
| Hamamelis extract | 10.0 |
| Boric acid | 0.5 |
| Product D | 10.0 |
| Water | 10.0 |

EXAMPLE 8

| Face Lotion | Parts by Weight |
| --- | --- |
| Cucumber essence | 15.0 |
| Citric acid | 0.2 |
| Ethanol 96% | 15.0 |
| Product A | 10.0 |
| Perfume | 1.0 |
| Water | 58.8 |

In place of these compounds used in accordance with the invention mentioned in the above examples, others of the products in accordance with the invention may be used with equally good success.

The preceding specific embodiments are illustrative of the practice of the invention. It is to be understood, however, that other expedients known to those skilled in the art, or given herein, may be employed without departing from the spirit of the invention or the scope of the appended claims.

We claim:

1. A process for the care and protection of the skin of warm-blooded animals comprising topically applying to the skin a safe but effective amount as moisturizing agent of a cosmetic moisturizing composition consisting essentially of from about 1% to about 20% by weight of at least one polyethercarboxylic acid compound having the formula $$R_1-O-CH_2-COOM$$

wherein M is selected from the group consisting of hydrogen, an alkali metal cation, an alkaline earth metal cation, ammonium ion, a lower-alkyl-ammonium ion, a lower alkanol-ammonium ion, and mixtures thereof, wherein $R_1$ is alkyl having 1 to 8 carbon atoms and having substitutents selected from the group consisting of carboxyl, hydroxyl and substituents group of the formula $-O-CH_2-COOM$, wherein M has the above-defined meanings, with the proviso that there are at least two carboxyl groups in the molecule of said acid compound and the remainder being inert cosmetic excipients for the care and protection of the skin.

2. A process for the care and protection of the skin of warm-blooded animals comprising topically applying to the skin a safe but effective amount as moisturizing agent of a cosmetic moisturizing composition consisting essentially of an emulsion adjusted to a pH between 5 and 7 containing from about 1% to about 20% by weight, based upon the total weight of the composition, of at least one polyethercarboxylic acid compound having the formula $$R_1-O-CH_2-COOM$$

wherein M is selected from the group consisting of hydrogen, an alkali metal cation, an alkaline earth metal cation, ammonium ion, a lower-alkyl-ammonium ion, a lower-alkyl-ammonium ion, a lower-alkanol-ammonium ion, and mixtures thereof, wherein $R_1$ is alkyl having 1 to 8 carbon atoms and having substituents selected from the group consisting of carboxyl, hydroxyl and a group of the formula $$O-CH_2-COOM,$$

wherein M has the above-defined meanings, with the proviso that there are at least two carboxyl groups in the molecule of said acid compound, and the remainder being inert cosmetic excipients for the care and protection of the skin, said emulsion being selected from the group consisting of oil-in-water emulsions and water-in-oil emulsions.

3. A process for the care and protection of the skin of warm-blooded animals comprising topically applying to the skin a safe but effective amount as moisturizing agent of a cosmetic moisturizing composition consisting essentially of a water and ethanol solution adjusted to a pH between 5 and 7 containing from about 1% to about 20% by weight, based upon the total weight of the composition, of at least one polyethercarboxylic acid compound having the formula $$R_1-O-CH_2-COOM,$$

wherein M is selected from the group consisting of hydrogen, an alkali metal cation, an alkaline earth metal cation, ammonium ion, a lower-alkyl-ammonium ion, a lower-alkanol-ammonium ion, and mixtures thereof, wherein $R_1$ is alkyl having 1 to 8 carbon atoms and having substituents selected from the group consisting of carboxyl, hydroxyl and a group of the formula $$O-CH_2-COOM,$$

wherein M has the above-defined meanings, with the proviso that there are at least two carboxl groups in the molecule of said acid compound, and the remainder being inert cosmetic excipients for the care and protection of the skin.

* * * * *

UNITED STATES PATENT AND TRADEMARK OFFICE
CERTIFICATE OF CORRECTION

PATENT NO. : 4,153,726
DATED : May 8, 1979
INVENTOR(S) : GERHARD BORGGREFE et al.

It is certified that error appears in the above-identified patent and that said Letters Patent are hereby corrected as shown below:

Column 2, line 46 "interg-" should read --integ- --.
Column 3, line 25, "salts as" should read -- salts such as --;
         line 41, "hydroscopicity" should read
                  -- hygroscipicity --.
Column 5, line 18, "unit" should read -- units --;
         line 22, "has" should read -- had --.
Column 8, line 35, "and substituents" should read -- and a --;
         line 57, delete "a lower alkyl-ammonium ion --
                  (second occurrence).
Column 10, line 15, "carboxl" should read -- carboxyl --.

Signed and Sealed this

Twelfth Day of February 1980

[SEAL]

Attest:

SIDNEY A. DIAMOND

Attesting Officer

Commissioner of Patents and Trademarks